United States Patent
Jin et al.

(10) Patent No.: US 10,570,520 B2
(45) Date of Patent: Feb. 25, 2020

(54) PREPARATION OF CONJUGATED DIMER AND PRODUCTS FORMED THEREFROM

(71) Applicant: KEMET Electronics Corporation, Simpsonville, SC (US)

(72) Inventors: Yang Jin, Jiangsu (CN); Qingping Chen, Simpsonville, SC (US)

(73) Assignee: KEMET Electronics Corporation, Fort Lauderdale, FL (US)

( * ) Notice: Subject to any disclaimer, the term of this patent is extended or adjusted under 35 U.S.C. 154(b) by 123 days.

(21) Appl. No.: 15/897,276

(22) Filed: Feb. 15, 2018

(65) Prior Publication Data

US 2018/0211788 A1    Jul. 26, 2018

Related U.S. Application Data

(62) Division of application No. 14/470,319, filed on Aug. 27, 2014, now Pat. No. 9,928,964.

(60) Provisional application No. 61/870,848, filed on Aug. 28, 2013.

(51) Int. Cl.
| | |
|---|---|
| *C23C 28/00* | (2006.01) |
| *C07D 409/14* | (2006.01) |
| *C08G 75/06* | (2006.01) |
| *C25B 3/00* | (2006.01) |
| *H01G 9/15* | (2006.01) |
| *H01G 9/042* | (2006.01) |

(52) U.S. Cl.
CPC ............ *C23C 28/00* (2013.01); *C07D 409/14* (2013.01); *C08G 75/06* (2013.01); *C25B 3/00* (2013.01); *H01G 9/0425* (2013.01); *H01G 9/15* (2013.01)

(58) Field of Classification Search
CPC ....................................... C23C 28/00
USPC ................................. 528/377, 378
See application file for complete search history.

(56) References Cited

U.S. PATENT DOCUMENTS

| 8,101,709 | B1 * | 1/2012 | Kaner | ............... C08G 61/124 528/377 |
| 2005/0059730 | A1 * | 3/2005 | Ohba et al. | ............ C07D 49/02 514/444 |
| 2011/0315204 | A1 * | 12/2011 | Gleason et al. | ........ H01L 31/02 136/256 |

* cited by examiner

*Primary Examiner* — Duc Truong
(74) *Attorney, Agent, or Firm* — Joseph T. Guy; Patent Filing Specialist, Inc.

(57) ABSTRACT

An improved process for forming a conjugated thiophene precursor is described as in the formation of an improved polymer prepared from the conjugated thiophene and an improved capacitor formed from the improved polymer. The improved process includes forming a thiophene mixture comprising thiophene monomer, unconjugated thiophene oligomer, optionally a solvent and heating the thiophene mixture at a temperature of at least 100° C. to no more than the lower of 250° C. or the boiling point of a component of said thiophene mixture with the lowest boiling point temperature.

37 Claims, 6 Drawing Sheets

PREPARATION OF CONJUGATED DIMER AND PRODUCTS FORMED THEREFROM

CROSS-REFERENCE TO RELATED APPLICATIONS

This application claims priority to pending U.S. patent application Ser. No. 14/470,319 filed Aug. 27, 2014 now U.S. Pat. No. 9,928,964 which, in turn, claims priority to expired U.S. Provisional Application No. 61/870,848 filed Aug. 28, 2013 both of which are incorporated herein by reference in their entirety.

FIELD OF THE INVENTION

This invention relates to an improved method for forming conjugated dimers and oligomers of thiophenes and subsequent formation of improved polymers formed from the conjugated dimer and oligomers. The invention further includes improved capacitors formed from the improved polymers.

BACKGROUND OF THE INVENTION

Polythiophene polymers, and especially poly-(3,4-ethylenedioxythiophene) (PEDT) have been found to be a very favorable electrically conductive material for many systems wherein high conductivity in a coated layer is desired. Polythiophene polymers can be made by in-situ polymerization or formed separately and then used as a polymer slurry to coat a surface. The formation of the polymer from a monomer is known to include some fraction of dimer and oligomer formation wherein the dimer or oligomer is incorporated into the polymer chain. Incorporation of particularly, dimers has been found to be advantageous to the polymerization process. It has been known for some time that the dimer or oligomer formed under common conditions of in situ polymerization is largely unconjugated and these unconjugated segments disrupt the conjugation within the polymer. There has therefore been a desire to eliminate, or at least significantly reduce, the formation of unconjugated dimers and oligomers even though this has proven quite difficult.

Purposefully and preferentially synthesizing the conjugated dimer and oligomer in high ratios requires very harsh chemicals and conditions, and is typically done by Ullmann coupling. Ullmann coupling is not a desirable reaction for use on a large manufacturing scale. Converting the non-conjugated dimer to the conjugated dimer has been described. However, this process requires a dehydrogenating agent and is not a practical process for a manufacturing environment, either.

Polythiophenes have gained a significant following in the art of electrolytic capacitors and polythiophenes are now commonly employed as the charge collecting layer, or cathode, in solid electrolyte capacitors. The incorporation of non-conjugated dimers and oligomers, and resulting loss of conductivity, is particularly bothersome for capacitors and the processes associated with purposeful synthesis of conjugated dimers or conversion of non-conjugated dimers to conjugated dimers has not been compatible with capacitors and capacitor manufacturing processes.

Both chemical and electrochemical polymerization has been used to form intrinsically conductive polymers for electrolytic capacitors. Chemical polymerization is well described in U.S. Pat. No. 4,910,645, to Jonas et. al., U.S. Pat. No. 6,136,176 to D. Wheeler, et. al. and U.S. Pat. No. 6,334,966 to Hahn et al. The process consists of immersing the anodized substrate first in a solution of an oxidizing agent such as, but not necessarily limited to, Fe (III) p-tosylate. After a drying step the anode bodies are then immersed in a solution of the monomer. Once the solution of monomer, which may consist entirely of monomer, is introduced into the capacitor anode bodies, the anodes are allowed to stand to facilitate production of the intrinsically conductive polymer material. Repeated dipping sequences may be employed to more completely fill the pore structure of the anode bodies and to cover the surface of the anode. In practice, rinsing cycles are generally employed to remove reaction by-products, such as ammonium sulfate, sulfuric acid, or iron salts when an iron (III) oxidizer is employed, or other by-products depending on the system employed.

When used in a capacitor a decrease in conjugation length of the polymer deteriorates the conductivity which causes an increase in equivalent series resistance (ESR) and leakage current. The acid present in the oxidizer, and as a by-product of the polymerization, promotes the formation of non-conjugated linkages in the polymer. In U.S. Pat. No. 7,754,276 procedures to control the acid content in the monomer solution are disclosed. Although the conductivity of polymer made according to U.S. Pat. No. 7,754,276 remained high, the growth rate of the conductive polymer could be decreased. More production cycles may be required to provide adequate polymer coverage.

Chemical production of intrinsically conductive organic polymers may also be carried-out on capacitor anode bodies by first introducing the monomer to the capacitor bodies, followed by introduction of the oxidizer and dopant which is the reverse order of polymer precursor introduction described above. It is also known to mix the dopant acid(s) with the monomer solution rather than with the oxidizer solution if this is found to be advantageous. U.S. Pat. Nos. 6,001,281 and 6,056,899 describe a chemical means of producing an intrinsically conductive organic polymer through the use of a single solution which contains both the monomer and the oxidizing agent, which has been rendered temporarily inactive via complexing with a high vapor pressure solvent. As the solution is warmed and the inhibiting solvent evaporates, the oxidative production of conductive polymers ensues. The dopant acid anion is also contained in the stabilized poly-precursor solution.

Intrinsically conductive organic polymers generally contain one dopant anion for each 3 to 4 monomer units which have been joined to form the polymer. The presence of a strong dopant acid anion is thought to result in a delocalization of electric charge on the conjugated molecular chain and therefore provides electrical conductivity. In the case of a ferric salt being used as the oxidizer, the presence of an acid also keeps the $Fe^{3+}$ ions from precipitating out of the solution. In the sequential dipping process the acid could accumulate in the monomer solution. It is known that an acid can promote the formation of non-conjugated dimers and trimers through acid catalyzed reaction. U.S. Pat. No. 6,891,016 to Reuter et al. disclosed the formation of non-conjugated ethylenedioxythiophene (EDT) dimer, and trimer in the presence of an acid catalyst.

There has been a long standing need for a process for forming a conductive polymer, and particularly a polythiophene, with a low number of unconjugated sections. Such a process is provided herein.

SUMMARY OF THE INVENTION

It is an object of the present invention to provide a way of making conjugated dimer and oligomer which is friendly to large scale manufacturing.

It is another object to provide an improved conductive polymer with reduced resistance by utilizing the conjugated dimer.

It is yet another object of the present invention to provide an improved capacitor wherein the capacitor has a lower ESR due to a lower resistance in the polymeric cathode layer.

A particular advantage of the present invention is the ability to implement the improvement with minimal alterations to existing manufacturing facilities or processes.

These and other advantages, as will be understood, are provided in a process for forming a conjugated thiophene precursor. The process includes forming a thiophene mixture comprising thiophene monomer, unconjugated thiophene oligomer and, optionally a solvent and heating the thiophene mixture at a temperature of at least 100° C. to no more than about 250° C., or the upper limit not to exceed the boiling point of monomer or the solvent Yet another embodiment is provided in a process for forming a polymer comprising: forming an conjugated thiophene precursor by a process comprising: forming a thiophene mixture comprising thiophene monomer, unconjugated thiophene oligomer, optionally a solvent; and heating the thiophene mixture at a temperature of at least 100° C. to no more than 250° C. followed by polymerizing the conjugated thiophene precursor.

Yet another embodiment is provided in a process for forming a capacitor comprising: forming an anode with a dielectric on said anode; forming a conjugated thiophene precursor comprising: forming a thiophene mixture comprising thiophene monomer, unconjugated thiophene oligomer, optionally a solvent; and heating the polythiophene mixture at a temperature of at least 100° C. to no more than 250° C. and forming a layer of a polymer of the conjugated thiophene precursor on the dielectric.

DETAILED DESCRIPTION

Figure 1:
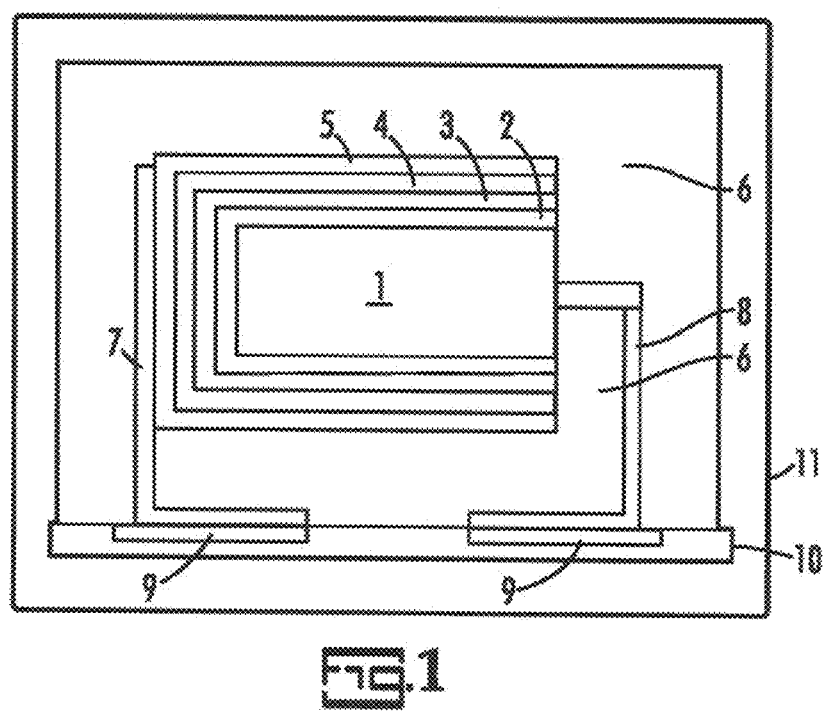
FIG. 1 is a schematic cross-sectional view of a capacitor of the present invention.

An improvement in a conductive polymer, and capacitor formed with the conductive polymer, is achieved by converting non-conjugated dimer and oligomer to conjugated dimer and oligomer, and forming a polymer with the dimers and oligomers which are rich in conjugated dimers and oligomers.

The invention includes heating, or preheating, a mixture of monomeric thiophene and non-conjugated thiophene dimer or oligomer at a temperature of 100 up to 250° C. or the boiling point of the solvent or monomer or component with the lowest boiling point, preferably in a solvent and preferably for at least 1 hour to preferably 24 hours thereby forming a polymer precursor. The precursor is then polymerized resulting in a polymer with improved conductivity. While not limited to any theory it is hypothesized that the pre-heat treatment accelerates the irreversible transition from non-conjugated to conjugated dimers and oligomers which lead to an increased degree of conjugation. When used as a cathode coating on capacitors the increased degree of conjugation is believed to improve coating quality resulting in an improved capacitor.

The oxidizer is selected from Fe(III) salts of organic and inorganic acids, alkali metal persulfates, ammonium persulfates and others. The preferred oxidant is Fe(III) p-tosylate or $Fe(O-SO_2C_6H_4CH_3)_3$.

The solvent may be any suitable solvent in which monomer and the oxidant are soluble, including, but not limited to, alcohols, ketones, esters, ethers. Preferably, the solvent is ethanol.

The polymer precursors are polymerized to form the conductive layer which may then be used as the cathode of the capacitor. The polymer precursors are preferably polymerized by either electrochemical or chemical polymerization techniques with oxidative chemical polymerization being most preferred. In one embodiment the conductive layer is formed by dipping the anodized substrate first in a solution of an oxidizing agent such as, but not necessarily limited to Fe (III) p-tosylate. After a drying step, the anode bodies are then immersed in a solution comprising monomer and oligomers of the conductive polymer and solvents.

The present invention utilizes a polymer precursor comprising a monomer and conjugated dimer or oligomer made by treating the non-conjugated dimer. The monomer preferably represents 75-99.9 wt % of the polymer precursors and the conjugated oligomer represents 0.1-25 wt % of the polymer precursors. More preferably the monomer represents 90-99.9 wt % of the polymer precursors and the conjugated oligomer represents 0.1-10 wt % of the polymer precursors. Even more preferably the monomer represents 95-99.5 wt % of the polymer precursors and the conjugated oligomer represents 0.5-5 wt % of the polymer precursors. The preferred monomer is a compound of Formula I and the preferred oligomer is a compound of Formula II.

The conducting polymer is preferably the polymer comprising repeating units of a monomer and oligomer of Formula I and Formula II:

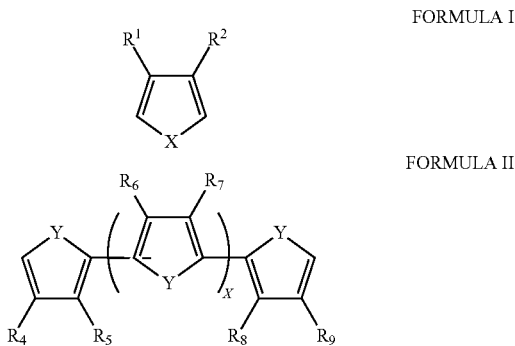

wherein the oligomer of FORMULA III is prepared from an oligomer defined by Formula III

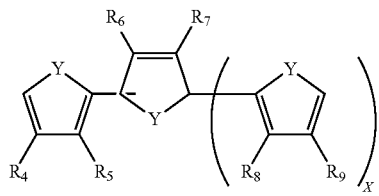

FORMULA III and wherein $R^1$ and $R^2$ of Formula I and $R^4$-$R^9$ of Formulas II and III are chosen to prohibit polymerization at the β-site of the ring. It is most preferred that only α-site polymerization be allowed to proceed. Therefore, it is preferred that $R^1$ and $R^2$ are not hydrogen. More preferably $R^1$, $R^2$, $R^4$, $R^5$, $R^6$, $R^7$, $R^8$ and $R^9$ are α-directors. Therefore, ether linkages are preferable over alkyl linkages. It is most preferred that the groups are small to avoid steric interferences. For these reasons $R^1$ and $R^2$, $R^4$ and $R^5$, $R^6$ and $R^7$ or $R^8$ and $R^9$ taken together as —O—(CH$_2$)$_2$—O— are most preferred.

In Formula II and III subscript X is an integer selected from 0-3.

In Formula I atom X and in Formula II atom Y independently are S, Se or N. Most preferably X and Y are S.

$R^1$, $R^2$, $R^4$, $R^5$, $R^6$, $R^7$, $R^8$ and $R^9$ independently represent linear or branched $C_1$-$C_{16}$ alkyl or $C_1$-$C_{18}$ alkoxyalkyl; or are $C_3$-$C_8$ cycloalkyl, phenyl or benzyl which are unsubstituted or substituted by $C_1$-$C_6$ alkyl, $C_1$-$C_6$ alkoxy, halogen or $OR^3$; or $R^1$ and $R^2$, $R^4$ and $R^5$, $R^6$ and $R^7$ or $R^8$ and $R^9$, taken together, are linear $C_1$-$C_6$ alkylene which is unsubstituted or substituted by $C_1$-$C_6$ alkyl, $C_1$-$C_6$ alkoxy, halogen, $C_3$-$C_5$ cycloalkyl, phenyl, benzyl, $C_1$-$C_4$ alkylphenyl, $C_1$-$C_4$ alkoxyphenyl, halophenyl, $C_1$-$C_4$ alkylbenzyl, $C_1$-$C_4$ alkoxybenzyl or halobenzyl, 5-, 6-, or 7-membered heterocyclic structure containing two oxygen elements. $R^3$ preferably represents hydrogen, linear or branched $C_1$-$C_{16}$ alkyl or $C_1$-$C_{18}$ alkoxyalkyl; or are $C_3$-$C_8$ cycloalkyl, phenyl or benzyl which are unsubstituted or substituted by $C_1$-$C_6$ alkyl.

More preferably $R^1$, $R^2$, $R^4$, $R^5$, $R^6$, $R^7$, $R^8$ and $R^9$, independently of one another, represent —CH$_3$, —CH$_2$CH$_3$; —OCH$_3$; —OCH$_2$CH$_3$ or most preferably $R^1$ and $R^2$, $R^4$ and $R^5$, $R^6$ and $R^7$ or $R^8$ and $R^9$ are taken together to represent —CH$_2$CH$_2$— wherein the hydrogen can be replaced with a solubilizing group, a halide or an alkyl.

Terms and chemical formulas used herein to refer to alkyl or aryl moieties refer to either the substituted or unsubstituted unless specifically stated otherwise. A solvent is defined as a single solvent or a mixture of solvents.

The synthesis of conjugated dimers and trimers is well known in the literature. For example. The dimer of EDT can be made through Ullmann coupling of the monomers with alkyl lithium and cupric chloride [J. Kagan and S. K. Arora, Heterocycles, 20 (1983) 1937].

Figure 2A:
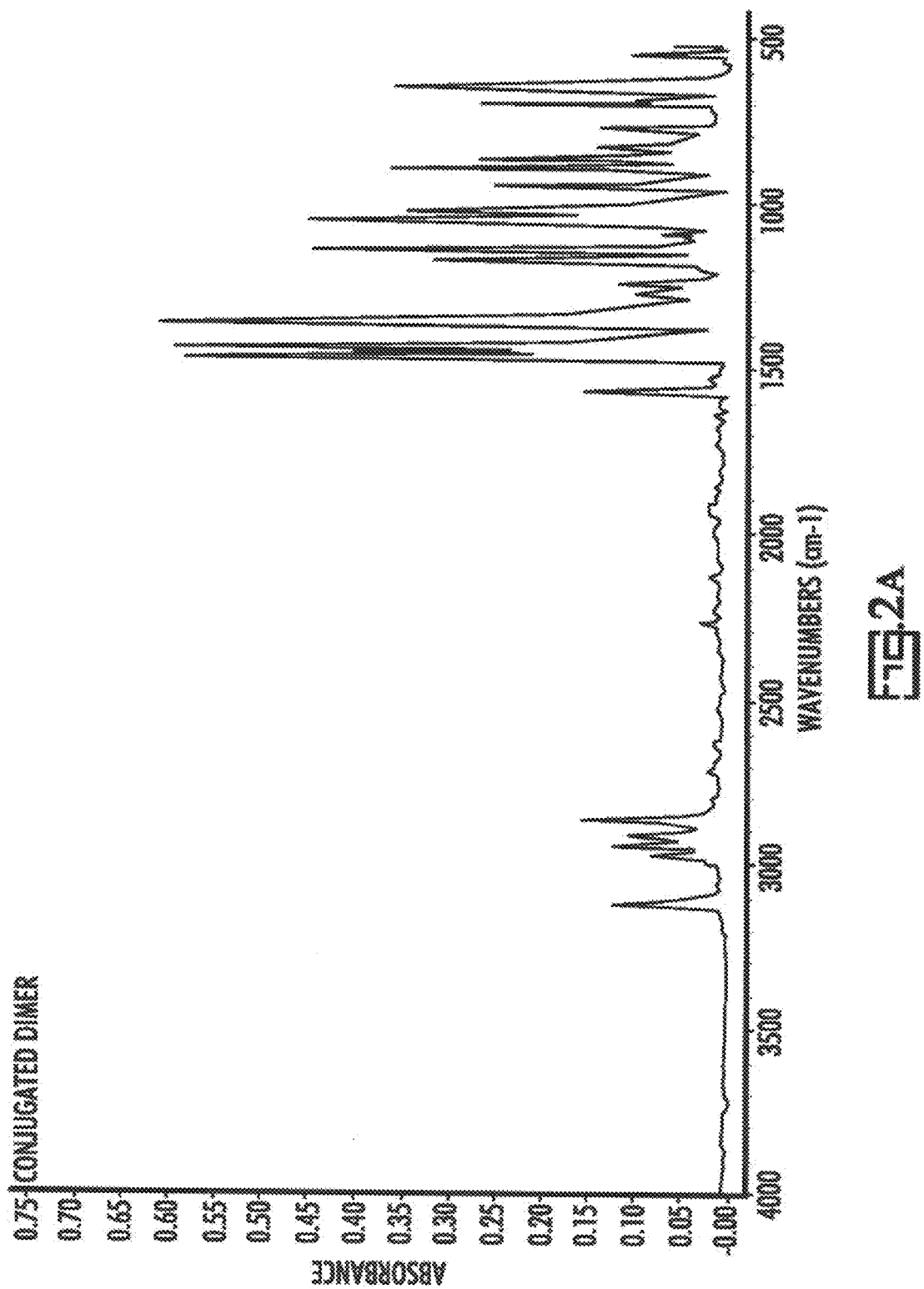
FIGS. 2a and 2b provide Fourier transform infrared (FT-IR) spectra of conjugated and nonconjugated EDT dimers, respectively.
Figure 2B:
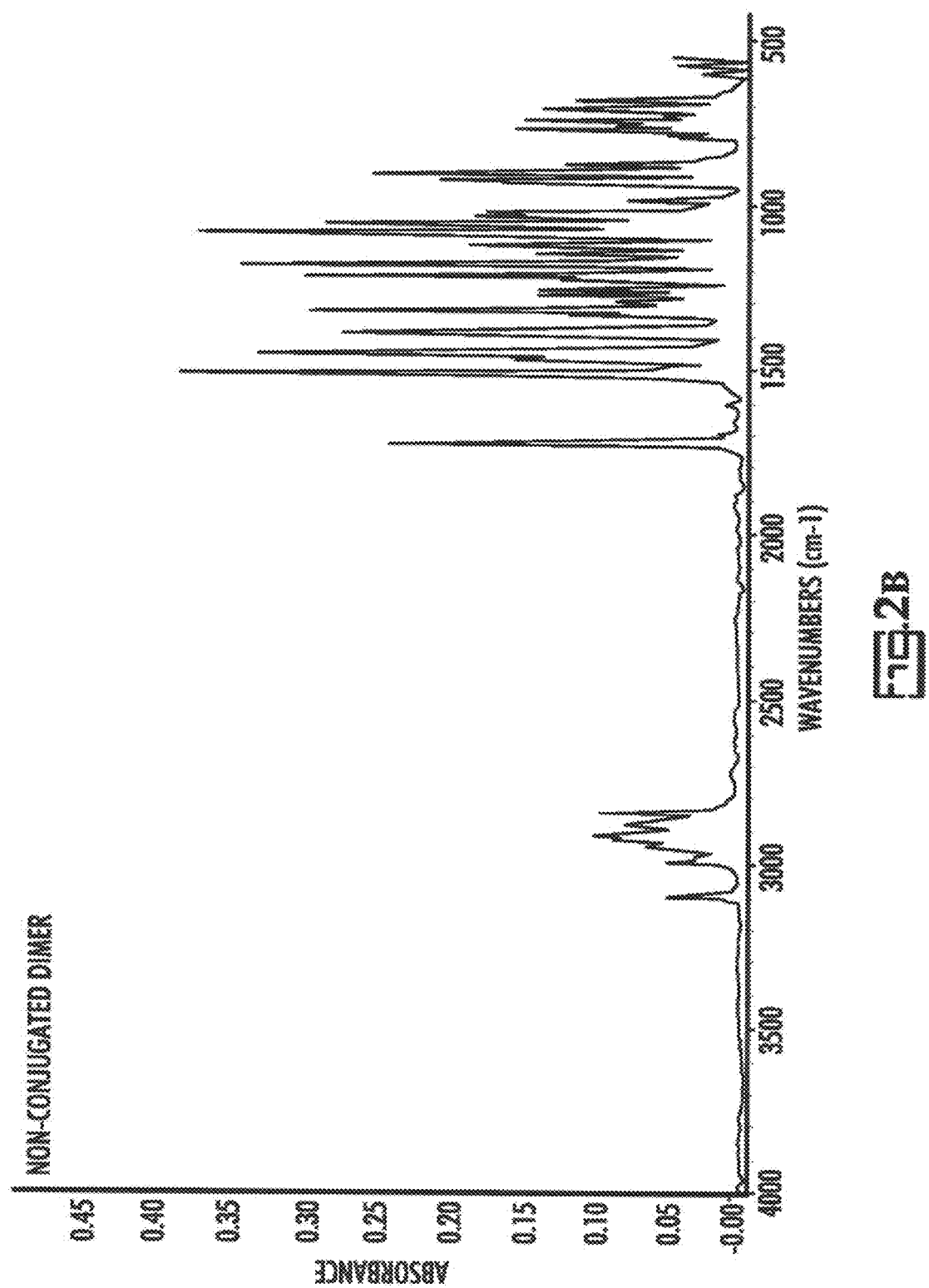
Figure 3A:
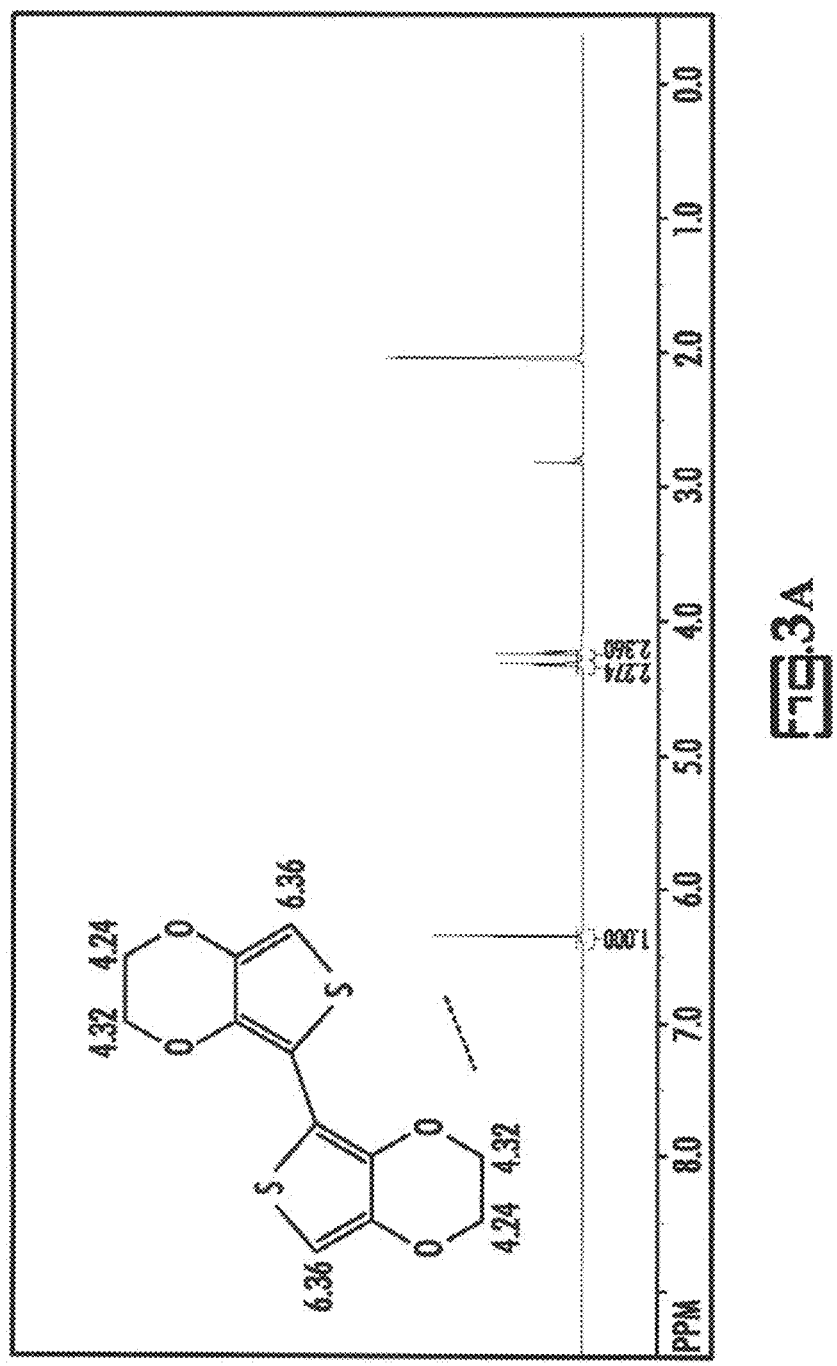
FIGS. 3a and 3b provide proton nuclear magnetic resonance ($^1$H NMR) spectra of conjugated and nonconjugated EDT dimers, respectively.
Figure 3B:
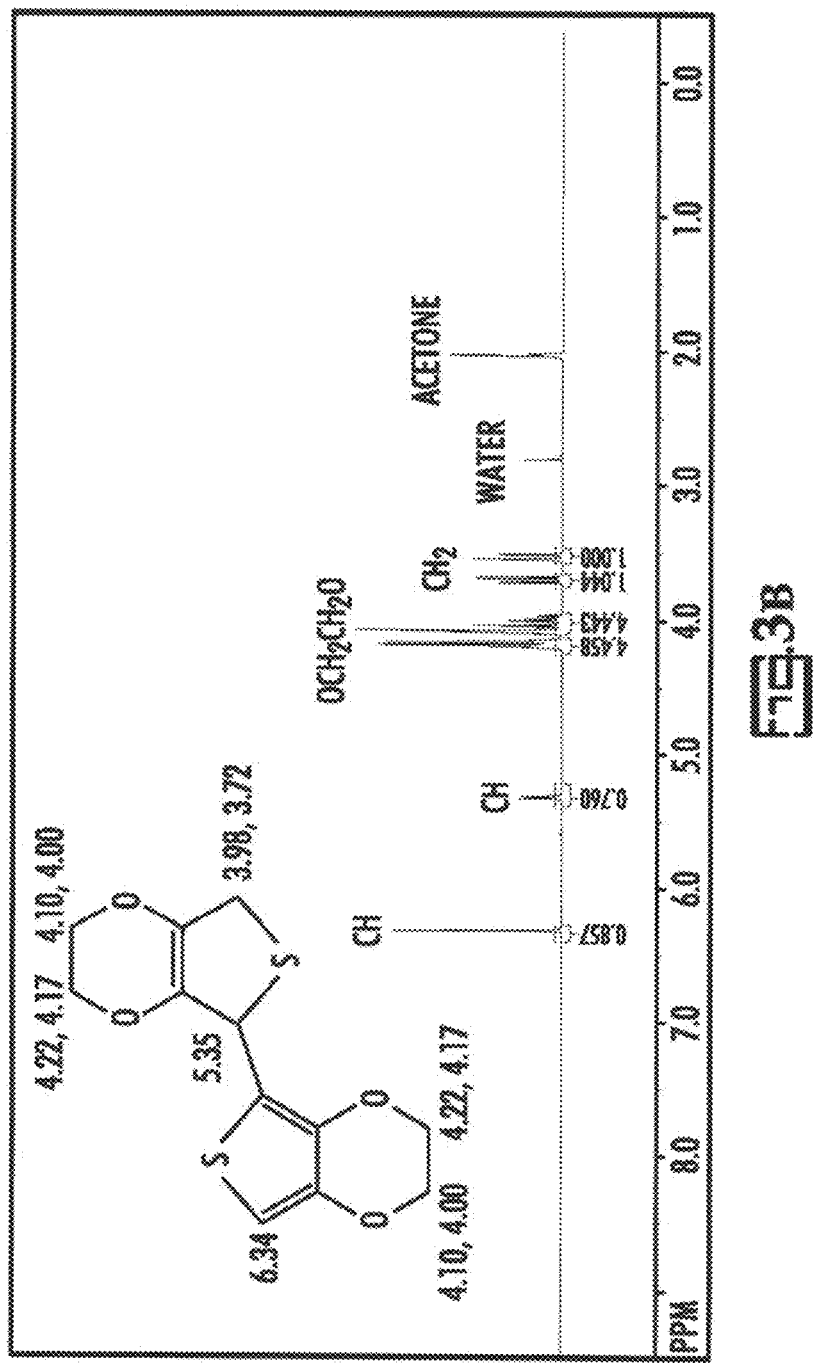
Figure 4:
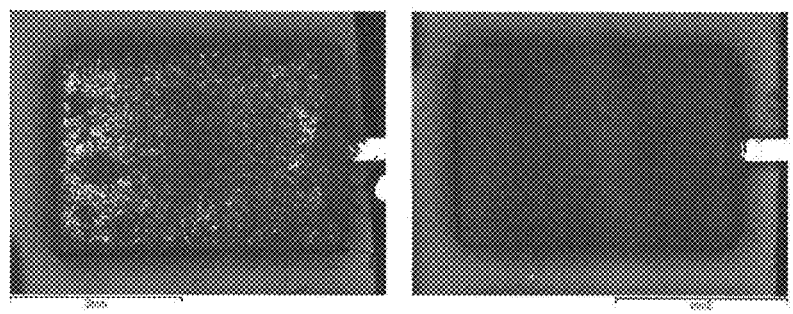
FIG. 4 illustrates an embodiment of the invention.

Conjugated and non-conjugated dimers can be distinguished by FT-IR spectroscopy as illustrated in FIG. 2, and by NMR spectroscopy as illustrated in FIG. 3. The presence of nonconjugated dimer in a sample of EDT that was used in the manufacturing dip process of making PEDT onto an anodized Ta surface is shown in FIG. 4. The content of the conjugated as well as non-conjugated dimers in the monomer can be measured by gas chromatograph (GC). Using EDT as an example, the peaks for the monomer, non-conjugated dimer, and conjugated dimer are distinguishable. It is observed over time that the peak for non-conjugated dihydrothiophene, grows in intensity during usage. Increased acid as a by-product of the polymerization may be the cause of the increase of non-conjugated dimer.

The invention will be described with reference to FIG. 1 forming a part of the present application.

In FIG. 1, a cross-sectional view of a capacitor is shown. The capacitor comprises an anode, 1. A dielectric layer, 2, is provided on the surface of the anode, 1. The dielectric layer is preferably formed as an oxide of the anode as further described herein. Coated on the surface of the dielectric layer, 2, is a conducting layer, 3. Layers 4 and 5 are conductive coating layers comprising graphite and silver based materials and providing connection to lead 7. Leads, 7 and 8, provide contact points for attaching the capacitor to a circuit. The entire element, except for the terminus of the leads, is then preferably encased in a housing, 6, which is preferably an epoxy resin housing. The capacitor may be attached to circuit traces, 9, of a substrate, 10, and incorporated into an electronic device, 11.

The anode is a conductive material preferably comprising a valve-metal preferably selected from niobium, aluminum, tantalum, titanium, zirconium, hafnium, or tungsten or a conductive oxide such as NbO. Aluminum, tantalum, niobium and NbO are most preferred as the anode material. Aluminum is typically employed as a foil while tantalum, niobium and NbO are typically prepared by pressing a powder and sintering to form a compact. For convenience in handling, the anode is typically attached to a carrier thereby allowing large numbers of elements to be processed at the same time.

The anode in the form of a foil is preferably etched to increase the surface area. Etching is preferably done by immersing the anode into at least one etching bath. Various etching baths are taught in the art and the method used for etching the valve metal is not limiting herein.

A dielectric is formed on the anode. In a preferred embodiment the surface of the anode is coated with a dielectric layer comprising an oxide. It is most desirable that the dielectric layer be an oxide of the anode material. The oxide is preferably formed by dipping the anode into an electrolyte solution and applying a positive voltage. The process of forming the dielectric layer oxide is well known to those skilled in the art. Other methods of forming the dielectric layer may be utilized such as vapour deposition, sol-gel deposition, solvent deposition or the like. The dielectric layer may be an oxide of the anode material formed by oxidizing the surface of the anode or the dielectric layer may be a material which is different from the anode material and deposited on the anode by any method suitable therefore.

A complete coverage of the anodized surface by intrinsically conductive polymer is desired to prevent the graphite and other conductive layers of anode materials from contacting the bare surface of dielectric. When high leakage occurs on the dielectric surface intrinsically conductive polymers would degrade, lose the dopant induced delocalized charges and therefore become non-conductive. Through this mechanism intrinsically conductive polymers provide a self-healing protection similar to MnO$_2$ based solid electrolytic capacitors where MnO$_2$ would convert into the non-conductive Mn$_2$O$_3$ at elevated temperature.

The polymer coated capacitor anode bodies, coated with an intrinsically conductive organic polymer cathode layer, may then be processed into completed capacitors by coating the conductive polymer cathode coatings with graphite paint, conductive paint comprising conductive fillers such as silver particles, attachment of electrode leads, etc. as is well known to those skilled in the art. The device is incorporated into a substrate or device or it is sealed in a housing to form a discrete mountable capacitor as known in the art.

Other adjuvants, coatings, and related elements can be incorporated into a capacitor, as known in the art, without diverting from the present invention. Mentioned, as a non-limiting summary include, protective layers, multiple capacitive levels, terminals, leads, etc.

EXAMPLES

A sample vial was charged with 10 milliliter of EDT, commercially available as Clevios M V2, and 50 microliter of Fe (III) p-tosylate in ethanol available as Clevios C-E. The sample was placed for 10 hours in a reactor at room temperature. Ion exchange resin commercially available as LEWATIT® MP 62 WS, was then added to stop the polymerization reaction for several times. The final EDT solution was prepared by filtering the mixture. Heat treatment was then introduced to treat this solution. Non-conjugated and conjugated EDT dimer content was measured quantitatively by GC method. As shown in the Table 1 below, the heat treatment promotes the formation of conjugated dimer and finally the non-conjugated dimer content will be minor with suitable pre-heat condition. In addition, obvious solution appearance change will be observed, which may indicate the formation of EDT oligomers further.

TABLE 1

| Pre-heat condition | Non-conjugated dimer (% area) | Conjugated dimer (% area) | Ratio of Non-conjugated over Conjugated dimer |
|---|---|---|---|
| Control (room temperature) | 0.442 | 0.038 | 11.6 |
| 180 C., 1.5 hrs | 0.372 | 0.108 | 3.44 |
| 190 C., 1.5 hrs | 0.271 | 0.193 | 1.40 |
| 190 C., 6.0 hrs | 0.053 | 0.429 | 0.12 |

These prepared monomer solutions were further evaluated for use in the formation of the cathode in a solid electrolyte capacitor.

A series of identical capacitor precursors were prepared with a tantalum anode and tantalum oxide dielectric with 100 parts prepared for each example listed below. A poly (3,4-ethylenedioxythiophene) cathode was formed on the dielectric wherein for control samples the polymer was formed from a polymer precursor having about 2.0 wt % non-conjugated dimer and for the inventive samples the polymer was formed from a polymer precursor having about 2.0 wt % conjugated dimer. The data in Table 2 clearly shows that the addition of conjugated dimer into the monomer improved the polymer growth rate and the polymer coverage of the dielectric surface of the anodes while maintaining a low ESR. The improved coverage in turn helped to reduce the number of shorts.

TABLE 2

| Polymerization Condition | Polymer Coverage | ESR (Ohm) | Number of Shorts |
|---|---|---|---|
| fresh monomer | poor | 0.031 | 10 |
| 2.0% non-conjugated dimer | good | 0.040 | 5 |
| 2.0% conjugated dimer | good | 0.030 | 0 |

Typical polymer coverage by using non-conjugated and preheated precursor systems with the same dimer level is shown in FIG. 4 wherein the polymer coverage on a tantalum oxide surface of a tantalum anode is illustrated with non-conjugated polymer on the left and conjugated polymer on the right. Significantly improved polymer build-up on the dielectric surface can be observed after three polymerization cycles. The comparative example showed poor coverage with many electrical shorts post encapsulation. With two additional polymerization cycles, the non-conjugated system did produce comparable polymer coverage, however additional cycles increases production cost significantly. Further electrical parameters of the capacitors are shown in Table 3. Even with 2 fewer polymerization cycles the heated precursor can still be maintained at similar levels as the control.

TABLE 3

| | Polymerization Cycle | Capacitance (uF) | DF (%) | ESR (ohms) | Leakage (uA) |
|---|---|---|---|---|---|
| Non-conjugated system | 5 | 300.8 | 2.5 | 24.9 | 532 |
| Conjugated system | 3 | 298.9 | 2.4 | 26.7 | 511 |

The invention has been described with reference to the preferred embodiments without limit thereto. Additional embodiments, alterations and improvements could be envisioned without departure from the meets and bounds of the invention as more specifically set forth in the claims appended hereto.

The invention claimed is:

1. A process for forming a conjugated thiophene precursor comprising:
   forming a thiophene mixture comprising thiophene monomer, unconjugated thiophene oligomer; and
   heating said thiophene mixture at a temperature of at least 100° C. to no more than the lower of 250° C. or the boiling point of a component of said thiophene mixture with the lowest boiling point temperature.

2. The process for forming a conjugated thiophene of claim 1 wherein said thiophene monomer is defined by Formula I:

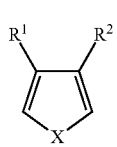

Formula I wherein $R^1$ and $R^2$ are independently α-directors; and
X is sulphur.

3. The process for forming a conjugated thiophene of claim 2 wherein $R^1$ and $R^2$ independently represent hydrogen, linear or branched $C_1$-$C_{16}$ alkyl or $C_1$-$C_{18}$ alkoxyalkyl; $C_3$-$C_8$ cycloalkyl; phenyl or benzyl which are unsubstituted or substituted by $C_1$-$C_6$ alkyl, $C_1$-$C_6$ alkoxy, halogen or —$OR^3$; or $R^1$ and $R^2$, taken together, are linear $C_1$-$C_6$ alkylene which is unsubstituted or substituted by $C_1$-$C_6$ alkyl, $C_1$-$C_6$ alkoxy, halogen, $C_3$-$C_8$ cycloalkyl, phenyl, benzyl, $C_1$-$C_4$ alkylphenyl, $C_1$-$C_4$ alkoxyphenyl, halophenyl, $C_1$-$C_4$ alkylbenzyl, $C_1$-$C_4$ alkoxybenzyl or halobenzyl, 5-, 6-, or 7-membered heterocyclic structure containing two oxygen elements; and
$R^3$ represents hydrogen, linear or branched $C_1$-$C_{16}$ alkyl; $C_1$-$C_{18}$ alkoxyalkyl; $C_3$-$C_8$ cycloalkyl, phenyl; benzyl which are unsubstituted or substituted by $C_1$-$C_6$ alkyl.

4. The process for forming a conjugated thiophene of claim 2 wherein $R^1$ and $R^2$ are not hydrogen.

5. The process for forming a conjugated thiophene of claim 2 wherein $R^1$ and $R^2$ are ether linkages.

6. The process for forming a conjugated thiophene of claim 2 wherein $R^1$ and $R^2$ are taken together as —O—$(CH_2)_2$—O—.

7. The process for forming a conjugated thiophene of claim 1 wherein said unconjugated thiophene oligomer is defined by Formula III:

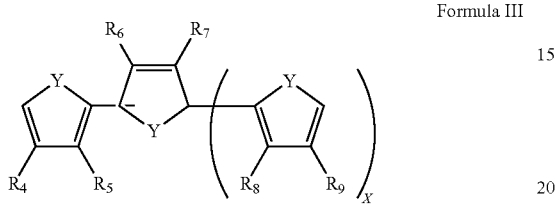

Formula III wherein:
X is an integer selected from 0-3;
$R_4$, $R_5$, $R_6$, $R_7$, $R_8$ and $R_9$ are independently α-directors; and
Y is sulphur.

8. The process for forming a conjugated thiophene of claim 7 wherein X is 0 or 1.

9. The process for forming a conjugated thiophene of claim 7 wherein $R_4$, $R_5$, $R_6$, $R_7$, $R_8$ and $R_9$ independently represent hydrogen, linear or branched $C_1$-$C_{16}$ alkyl or $C_1$-$C_{18}$ alkoxyalkyl; $C_3$-$C_8$ cycloalkyl, phenyl or benzyl which are unsubstituted or substituted by $C_1$-$C_6$ alkyl, $C_1$-$C_6$ alkoxy, halogen or —$OR^3$; or $R^4$ and $R^5$, $R^6$ and $R^7$ or $R^8$ and $R^9$, taken together, are linear $C_1$-$C_6$ alkylene which is unsubstituted or substituted by $C_1$-$C_6$ alkyl, $C_1$-$C_6$ alkoxy, halogen, $C_3$-$C_8$ cycloalkyl, phenyl, benzyl, $C_1$-$C_4$ alkylphenyl, $C_1$-$C_4$ alkoxyphenyl, halophenyl, $C_1$-$C_4$ alkylbenzyl, $C_1$-$C_4$ alkoxybenzyl or halobenzyl, 5-, 6-, or 7-membered heterocyclic structure containing two oxygen elements; and
$R^3$ represents hydrogen, linear or branched $C_1$-$C_{16}$ alkyl; $C_1$-$C_{18}$ alkoxyalkyl; $C_3$-$C_8$ cycloalkyl, phenyl; benzyl which are unsubstituted or substituted by $C_1$-$C_6$ alkyl.

10. The process for forming a conjugated thiophene of claim 7 wherein $R_4$, $R_5$, $R_6$, $R_7$, $R_8$ and $R_9$ are not hydrogen.

11. The process for forming a conjugated thiophene of claim 7 wherein $R_4$, $R_5$, $R_6$, $R_7$, $R_8$ and $R_9$ are ether linkages.

12. The process for forming a conjugated thiophene of claim 2 wherein $R_4$ and $R_5$, $R_6$ and $R_7$, and $R_8$ and $R_9$ are taken together as —O—$(CH_2)_2$—O—.

13. The process for forming a conjugated thiophene of claim 1 wherein said thiophene mixture further comprises a solvent.

14. The process for forming a conjugated thiophene of claim 13 wherein said solvent is selected from the group consisting of alcohols, ketones, esters and ethers.

15. The process for forming a conjugated thiophene of claim 13 comprising 10-90% by weight solvent.

16. The process for forming a conjugated thiophene of claim 1 wherein said thiophene mixture comprising 75-99.9 wt % thiophene monomer and 0.1 to 25 wt % unconjugated thiophene oligomer.

17. The process for forming a conjugated thiophene of claim 16 wherein said thiophene mixture comprising 90-99.9 wt % thiophene monomer and 0.1 to 10 wt % unconjugated thiophene oligomer.

18. A process for forming a polymer comprising:
forming an conjugated thiophene precursor by a process comprising:
forming a thiophene mixture comprising thiophene monomer, unconjugated thiophene oligomer and an oxidant; and
heating said polythiophene mixture at a temperature of at least 100° C. to no more than the lower of 250° C. or the boiling point of a component of said thiophene mixture with the lowest boiling point temperature; and
polymerizing said conjugated thiophene precursor.

19. The process for forming a polymer of claim 18 wherein said thiophene monomer is defined by Formula I:

Formula I wherein $R^1$ and $R^2$ are independently α-directors; and
X is sulphur.

20. The process for forming a polymer of claim 19 wherein $R^1$ and $R^2$ independently represent hydrogen, linear or branched $C_1$-$C_{16}$ alkyl or $C_1$-$C_{18}$ alkoxyalkyl; $C_3$-$C_8$ cycloalkyl; phenyl or benzyl which are unsubstituted or substituted by $C_1$-$C_6$ alkyl, $C_1$-$C_6$ alkoxy, halogen or —$OR^3$; or $R^1$ and $R^2$, taken together, are linear $C_1$-$C_6$ alkylene which is unsubstituted or substituted by $C_1$-$C_6$ alkyl, $C_1$-$C_6$ alkoxy, halogen, $C_3$-$C_8$ cycloalkyl, phenyl, benzyl, $C_1$-$C_4$ alkylphenyl, $C_1$-$C_4$ alkoxyphenyl, halophenyl, $C_1$-$C_4$ alkylbenzyl, $C_1$-$C_4$ alkoxybenzyl or halobenzyl, 5-, 6-, or 7-membered heterocyclic structure containing two oxygen elements; and
$R^3$ represents hydrogen, linear or branched $C_1$-$C_{16}$ alkyl; $C_1$-$C_{18}$ alkoxyalkyl; $C_3$-$C_8$ cycloalkyl, phenyl; benzyl which are unsubstituted or substituted by $C_1$-$C_6$ alkyl.

21. The process for forming a polymer of claim 19 wherein $R^1$ and $R^2$ are not hydrogen.

22. The process for forming a polymer of claim 19 wherein $R^1$ and $R^2$ are ether linkages.

23. The process for forming a polymer of claim 19 wherein $R^1$ and $R^2$ are taken together as —O—$(CH_2)_2$—O—.

24. The process for forming a polymer of claim 18 wherein said unconjugated thiophene oligomer is defined by Formula III:

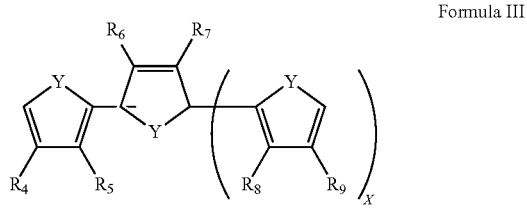

Formula III wherein:
X is an integer selected from 0-3;
$R_4$, $R_5$, $R_6$, $R_7$, $R_8$ and $R_9$ are independently α-directors; and
Y is sulphur.

25. The process for forming a polymer of claim 24 wherein X is 0 or 1.

26. The process for forming a polymer of claim 24 wherein $R_4$, $R_5$, $R_6$, $R_7$, $R_8$ and $R_9$ independently represent hydrogen, linear or branched $C_1$-$C_{16}$ alkyl or $C_1$-$C_{18}$ alkoxyalkyl; $C_3$-$C_8$ cycloalkyl, phenyl or benzyl which are unsubstituted or substituted by $C_1$-$C_6$ alkyl, $C_1$-$C_6$ alkoxy, halogen or —$OR^3$; or $R^4$ and $R^5$, $R^6$ and $R^7$ or $R^8$ and $R^9$, taken together, are linear $C_1$-$C_6$ alkylene which is unsubstituted or substituted by $C_1$-$C_6$ alkyl, $C_1$-$C_6$ alkoxy, halogen, $C_3$-$C_8$ cycloalkyl, phenyl, benzyl, $C_1$-$C_4$ alkylphenyl, $C_1$-$C_4$ alkoxyphenyl, halophenyl, $C_1$-$C_4$ alkylbenzyl, $C_1$-$C_4$ alkoxybenzyl or halobenzyl, 5-, 6-, or 7-membered heterocyclic structure containing two oxygen elements; and $R^3$ represents hydrogen, linear or branched $C_1$-$C_{16}$ alkyl; $C_1$-$C_{18}$ alkoxyalkyl; $C_3$-$C_8$ cycloalkyl, phenyl; benzyl which are unsubstituted or substituted by $C_1$-$C_6$ alkyl.

27. The process for forming a polymer of claim 24 wherein $R_4$, $R_5$, $R_6$, $R_7$, $R_8$ and $R_9$ are not hydrogen.

28. The process for forming a polymer of claim 24 wherein $R_4$, $R_5$, $R_6$, $R_7$, $R_8$ and $R_9$ are ether linkages.

29. The process for forming a polymer of claim 20 wherein $R_4$ and $R_5$, $R_6$ and $R_7$, and $R_8$ and $R_9$ are taken together as —O—$(CH_2)_2$—O—.

30. The process for forming a polymer of claim 18 wherein said thiophene mixture further comprises a solvent.

31. The process for forming a polymer of claim 30 wherein said solvent is selected from the group consisting of alcohols, ketones, esters and ethers.

32. The process for forming a polymer of claim 30 comprising 10-90% by weight solvent.

33. The process for forming a polymer of claim 18 wherein said thiophene mixture comprising 75-99.9 wt % thiophene monomer and 0.1 to 25 wt % unconjugated thiophene oligomer.

34. The process for forming a polymer of claim 33 wherein said thiophene mixture comprising 90-99.9 wt % thiophene monomer and 0.1 to 10 wt % unconjugated thiophene oligomer.

35. The process for forming a polymer of claim 18 wherein said polymerizing is by electrochemical polymerization.

36. The process for forming a polymer of claim 18 wherein said polymerizing is by chemical polymerization.

37. The process for forming a polymer of claim 36 wherein said chemical polymerization is oxidative chemical polymerization.

\* \* \* \* \*